United States Patent [19]

Meade et al.

[11] Patent Number: 5,900,228
[45] Date of Patent: May 4, 1999

[54] BIFUNCTIONAL DETECTION AGENTS HAVING A POLYMER COVALENTLY LINKED TO AN MRI AGENT AND AN OPTICAL DYE

[75] Inventors: Thomas J. Meade, Altadena; Scott E. Fraser, La Canada; Russell E. Jacobs, Arcadia, all of Calif.

[73] Assignee: California Institute of Technology, Pasadena, Calif.

[21] Appl. No.: 08/690,612

[22] Filed: Jul. 31, 1996

[51] Int. Cl.⁶ .......................... A61B 5/055; A61K 49/00
[52] U.S. Cl. ...................... 424/9.363; 424/9.362; 424/9.36; 424/9.3; 424/9.6; 424/9.61; 424/9.364; 424/9.365
[58] Field of Search .............. 424/9.323, 9.363, 424/9.364, 9.362, 9.3, 9.36, 9.322, 9.34, 9.35, 9.6, 9.61; 534/15, 16; 436/73, 81, 164, 173, 800, 805, 806

[56] References Cited

U.S. PATENT DOCUMENTS

| | | | |
|---|---|---|---|
| 4,637,988 | 1/1987 | Hinshaw et al. | 436/546 |
| 4,837,169 | 6/1989 | Toner | 436/546 |
| 4,877,872 | 10/1989 | Morgan | 540/145 |
| 5,095,099 | 3/1992 | Parkinson et al. | 534/15 |
| 5,230,883 | 7/1993 | Kornguth et al. | 424/9 |
| 5,292,414 | 3/1994 | Sessler et al. | 204/157.5 |
| 5,310,539 | 5/1994 | Williams | 424/9 |
| 5,338,532 | 8/1994 | Tomalia et al. | 424/1.49 |
| 5,466,438 | 11/1995 | Unger et al. | 424/9.365 |
| 5,622,821 | 4/1997 | Selvin et al. | 435/6 |

FOREIGN PATENT DOCUMENTS

95/20981   8/1995   WIPO .

OTHER PUBLICATIONS

Jacobs and Fraser, "Magnetic Resonance Microscopy of Embryonic Cell Lineages and Movements," *Science*, 263:681–684, Feb. 1994.

Staubli and Meade, "The Design and Synthesis of Fluorescently Detactable Magnetic Resonance imaging Agents for Embryonic Cell Lineage Analysis," *American Chemical Society: Division of Inorganic Chemistry*, 209th ACS National Meeting, Anaheim, California. Abstract No. 385 (Apr. 2–6, 1995).

*Primary Examiner*—Gary E. Hollinden
*Assistant Examiner*—Michael G. Hartley
*Attorney, Agent, or Firm*—Flehr Hohbach Test Albritton & Herbert LLP; Richard F. Trecartin; Robin M. Silva

[57] ABSTRACT

The invention provides bifunctional detection agents comprising optical dyes covalently linked to at least one magnetic resonance image (MRI) contrast agent. These agents may include a linker, which may be either a coupling moiety or a polymer.

20 Claims, 2 Drawing Sheets

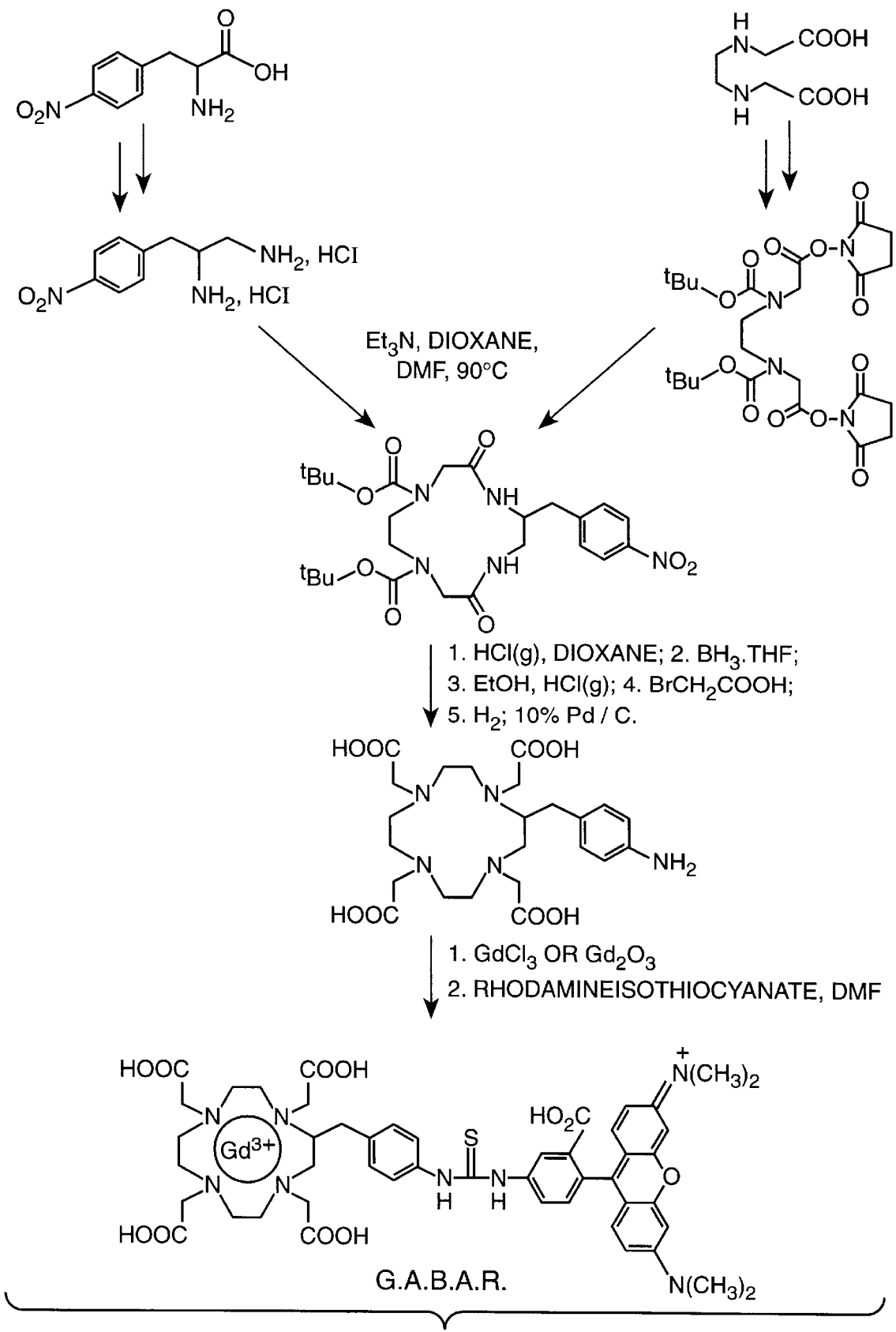
FIG._1

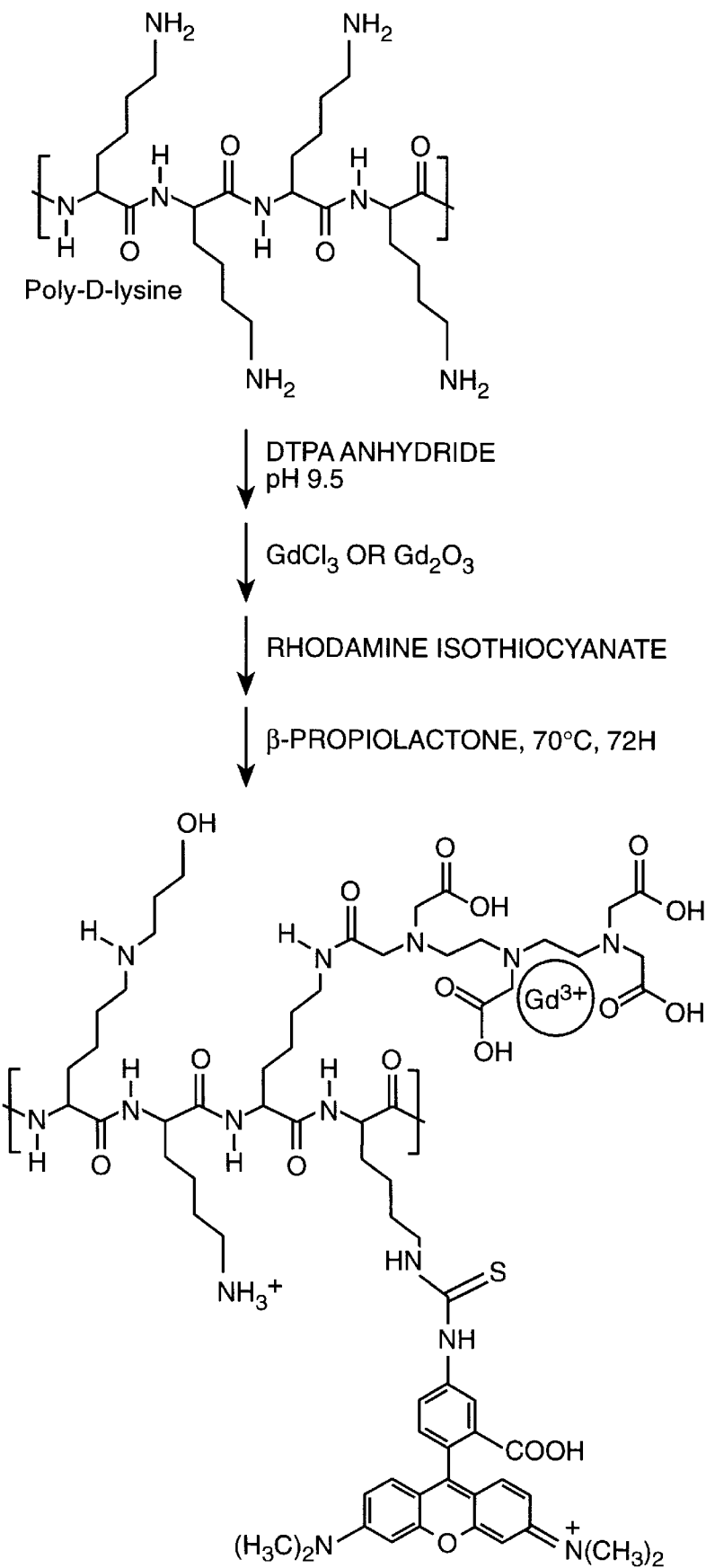
FIG._2

BIFUNCTIONAL DETECTION AGENTS HAVING A POLYMER COVALENTLY LINKED TO AN MRI AGENT AND AN OPTICAL DYE

The U.S. Government has certain rights in this invention pursuant to grant number DA 08944 from National Institutes of Health.

FIELD OF THE INVENTION

The invention relates to optically active magnetic resonance imaging agents.

BACKGROUND OF THE INVENTION

Magnetic resonance imaging (MRI) is a clinical diagnostic and research procedure that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI the sample to be imaged is placed in a strong static magnetic field (1–12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

There is rapidly growing body of literature demonstrating the clinical effectiveness of paramagnetic contrast agents; currently there are at least eight different contrast agents in clinical trials or in use. These agents provide further contrast, and thus enhanced images, wherever the contrast agent is found. For example, the approved contrast agents outlined below may be injected into the circulatory system and used to visualize vascular structures and abnormalities, amongst other things. The capacity to differentiate regions or tissues that may be magnetically similar but histologically different is a major impetus for the preparation of these agents.

The lanthanide atom Gd(III), has generally been chosen as the metal atom for contrast agents because it has a high magnetic moment ($\mu^2=63BM^2$), a symmetric electronic ground state, ($S^8$), the largest paramagnetic dipole and the greatest paramagnetic relaxivity of any element. Gd(III) is rendered nontoxic by chelation. To date, a number of chelators have been used, including diethylenetriaminepentaacetic (DTPA), 1,4,7,1 0-tetraazacyclododecane'-N,N'N",N'"-tetracetic acid (DOTA), and derivatives thereof. See U.S. Pat. Nos. 5,155,215, 5,087,440, 5,219,553, 5,188,816, 4,885,363, 5,358,704, 5,262,532, and Meyer et al., Invest. Radiol. 25:S53 (1990).

The stability constant (K) for GD(DTPA) is very high (logK=22.4) and is more commonly known as the formation constant (the higher the logK, the more stable the complex). This thermodynamic parameter indicates the fraction of Gd(III) ions that are in the unbound state will be quite small and should not be confused with the rate (kinetic stability) at which the loss of metal occurs. The water soluble Gd(DTPA)-chelate is stable, nontoxic, and one of the most widely used contrast enhancement agents in experimental and clinical imaging research. It was approved for clinical use in adult patients in June of 1988. It is an extracellular agent that accumulates in tissue by perfusion dominated processes. Image enhancement improvements using Gd(DTPA) are well documented in a number of applications (Runge et al., Magn, Reson. Imag. 3:85 (1991); Russell et al., AJR 152:813 (1989); Meyer et al., Invest. Radiol. 25:S53 (1990)) including visualizing blood-brain barrier disruptions caused by space occupying lesions and detection of abnormal vascularity. It has recently been applied to the functional mapping of the human visual cortex by defining regional cerebral hemodynamics (Belliveau et al., (1991) 254:719).

Another chelator used in Gd contrast agents is the macrocyclic ligand 1,4,7, 10-tetraazacyclododecane-N,N', N"N'"-tetracetic acid (DOTA). The Gd-DOTA complex has been thoroughly studied in laboratory tests involving animals and humans. The complex is conformationally rigid, has an extremely high formation constant (logK=28.5), and at physiological pH possess very slow dissociation kinetics. Recently, the GdDOTA complex was approved as an MRI contrast agent for use in adults and infants in France and has been administered to over 4500 patients.

Another technique for imaging cells, frequently used in developmental biology, uses optical dyes, i.e. photoluminescent compounds, to visualize both subcellular and extracellular structures, as well as developmental cell lineages.

It is an object of the invention to provide bifunctional detection agents that can simultaneously behave as both an optical dye as well as an MRI contrast agent. Such agents can be visualized using either MRI and common optical (photoluminescent) techniques.

SUMMARY OF THE INVENTION

In accordance with the objects outlined above, the present invention provides bifunctional detection agents comprising optical dyes covalently linked to at least one magnetic resonance image (MRI) contrast agent. These agents may include a linker, which may be either a coupling moiety or a polymer. These bifunctional detection agents include agents having the structure depicted below:

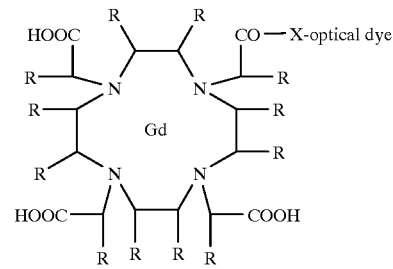

wherein X is a coupling moiety and R is a substitution moiety.

The invention also provides bifunctional detection agents having the structure:

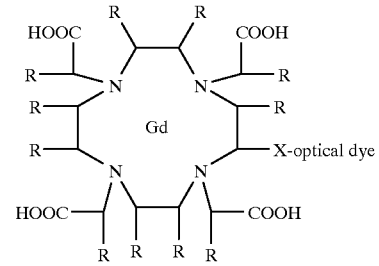

wherein X is a coupling moiety and R is a substitution moiety.

The invention additionally provides bifunctional detection agents having the structure:

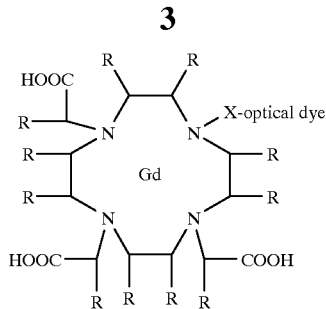

The invention further provides bifunctional detection agent comprising a polymer covalently linked to at least one optical dye and at least one MRI contrast agent. The polymer may comprise a polyamino acid. The polymer may have a molecular weight of less than 40 kD, 25 kD, 15 kD, or 10 kD.

The invention further provides methods of visualizing cells and tissues comprising the administration of the bifunctional detection agents with fluorescence and MRI detection.

BRIEF DESCRIPTION OF THE DRAWINGS

FIG. 1 shows the synthesis of GABAR (Gadolinium amino benzyl rhodamine) as described in the examples.

FIG. 2 shows the synthesis of GRP (Gadolinium rhodamine polylysine) as described in the examples.

DETAILED DESCRIPTION OF THE INVENTION

The present invention provides bifunctional detection agents that function as both magnetic resonance imaging (MRI) contrast agents as well as optically detectable agents or dyes.

In a preferred embodiment, the bifunctional detection agents comprise an MRI contrast agent covalently linked to a optical dye.

By "MRI contrast agent" herein is meant a molecule that can be used to enhance the MRI image. As is known in the art, MRI contrast agents generally comprise a paramagnetic metal ion bound to a chelator. By "paramagnetic metal ion", "paramagnetic ion" or "metal ion" herein is meant a metal ion which is magnetized parallel or antiparallel to a magnetic field to an extent proportional to the field. Generally, these are metal ions which have unpaired electrons; this is a term understood in the art. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In a preferred embodiment the paramagnetic ion is the lanthanide atom Gd(III), due to its high magnetic moment ($U^2$=63BM2), a symmetric electronic ground state (S8), and its current approval for diagnostic use in humans.

In addition to the metal ion, the MI contrast agent usually comprise a chelator. Due to the relatively high toxicity of many of the paramagnetic ions, the ions are rendered non-toxic in physiological systems by binding to a suitable chelator. The chelator utilizes a number of coordination atoms at coordination sites to bind the metal ion. As is more fully described below, the replacement of a coordination atom with a functional moiety to allow covalent attachment of the MRI contrast agent to a linker or optical dye may render the metal ion complex more toxic by decreasing the half-life of dissociation for the metal ion complex. Thus, in a preferred embodiment, a site other than a coordination site is preferably used for covalent attachment. However, for some applications, e.g. analysis of tissue and the like, the toxicity of the metal ion complexes may not be of paramount importance and thus covalent attachment via a coordination site is appropriate. Similarly, some metal ion complexes are so stable that even the replacement of one or more additional coordination atoms with a blocking moiety does not significantly effect the half-life of dissociation. For example, both DTPA and DOTA, described below, are extremely stable when complexed with Gd(III). Accordingly, one or several of the coordination atoms of the chelator may be replaced with one or more functional moieties for covalent attachment without a significant increase in toxicity.

There are a large number of known macrocyclic chelators or ligands which are used to chelate lanthanide and paramagnetic ions. See for example, Alexander, Chem. Rev. 95:273–342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25:S53 (1990), all of which are also expressly incorporated by reference. There are a variety of factors which influence the choice and stability of the chelate metal ion complex, including enthalpy and entropy effects (e.g. number, charge and basicity of coordinating groups, ligand field and conformational effects, etc.). In general, the chelator has a number of coordination atoms which are capable of binding the metal ion. The number of coordination atoms, and thus the structure of the chelator, depends on the metal ion. Thus, as will be understood by those in the art, any of the known paramagnetic metal ion chelators or lanthanide chelators can be easily modified using the teachings herein to add a functional moiety for covalent attachment to an optical dye or linker.

Preferred MRI contrast agents include, but are not limited to, 1,4,7,10-tetraazacyclododecane-N,N',N'',N'''-tetracetic acid (DOTA), diethylenetriaminepentaacetic (DTPA), 1,4,7,10-tetraazacyclododecane-N,N',N'',N'''-tetraethylphosphorus (DOTEP), 1,4,7,10-tetraazacyclododecane-N,N',N''-triacetic acid (Do3A) and derivatives thereof (see U.S. Pat. No. 5,188,816, 5,358,704, 4,885,363, and 5,219,553, hereby expressly incorporated by reference).

As is described herein, in a preferred embodiment the MRI agent is substituted at any number of possible positions with a functional group to facilitate the covalent attachment of the optical dye or linker such as a coupling moiety or polymer. For example, when the contrast agent is DOTA, a preferred embodiment utilizes any one of the R sites of structure 1 as the site of covalent attachment.

Structure 1

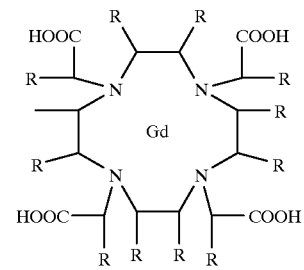

In an additional embodiment, one of the carboxylic acid chelating "arms" (i.e. a coordination atom) of DOTA may also be used as the site of covalent attachment, as depicted in Structure 2 (unsubstituted DOTA, although substituted compounds as also included:

Structure 2

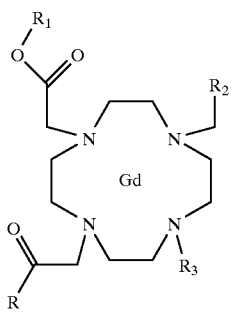

In this embodiment, either a carbonyl (i.e. as depicted with R in Structure 2), an ester linkage (i.e. as depicted with $R_1$), or direct linkage to the nitrogen atom (as depicted in $R_2$ and $R_3$) may be formed, depending on the type of coupling chemistry used, as is more generally outlined below. As will be appreciated by those in the art, similar substitutions may be done with DTPA and DOTEP (the unsubstituted forms of which are depicted in Structures 3 and 4, respectively, although as outlined above in Structure 1, the carbon atoms of DTPA and DOTEP or any other MRI agent of use herein may be substituted with R groups):

Structure 3

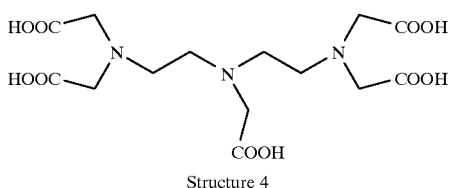

Structure 4

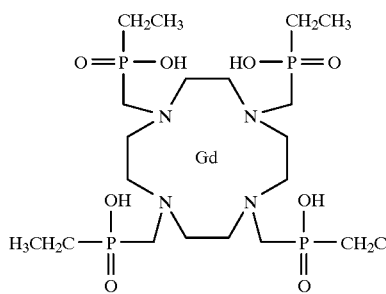

Other suitable Gd(III) chelators are described in Alexander, supra, Jackels, supra, Lauffer et al., supra, U.S. Pat. Nos. 5,155,215, 5,087,440, 5,219,553, 5,188,816, 4,885,363, 5,358,704, 5,262,532, and Meyer et al., Invest. Radiol. 25:S53 (1990), among others.

As will be appreciated by those in the art, the R sites outlined herein may also comprise additional substitution groups, in addition to the R site that is used for covalent attachment. Suitable substitution groups include a wide variety of groups, as will be understood by those in the art. For example, suitable substitution groups include substitution groups disclosed for DOTA and DOTA-type compounds in U.S. Pat. Nos. 5,262,532, 4,885,363, amd 5,358, 704. These groups include hydrogen, alkyl and aryl groups, substituted alkyl and aryl groups, amino groups, hydroxy groups, thiol groups, phosphorus moieties, etc. Preferred substitution groups include hydrogen. As will be appreciated by those skilled in the art, each position outlined herein may have two R groups attached (R' and R"), although in a preferred embodiment only a single R group is attached at any particular position. Thus, for example, the MRI contrast agents utilized in the invention may be substituted at any one of the R positions with moieties to confer or neutralize charge, alter the hydrophobicity or hydrophilicity, or alter the molecular weight. The larger the molecule, the slower it rotates in solution and the relaxivity increases.

Chelators for use with other metals are known. For example, suitable chelators for Fe(III) ions are well known in the art. See Lauffer et al., J. Am. Chem. Soc. 109:1622 (1987); Lauffer, Chem. Rev. 87:901–927 (1987); and U.S. Pat. Nos. 4,885,363, 5,358,704, and 5,262,532, all which describe chelators suitable for Fe(III). Suitable chelators for Mn(II) ions are also well known in the art; see for example Lauffer, supra, and U.S. Pat. Nos. 4,885,363, 5,358,704, and 5,262,532. Suitable chelators for Yt(III) ions include, but are not limited to, DOTA and DPTA and derivatives thereof (see Moi et al., J. Am. Chem. Soc. 110:6266–6267 (1988)) and those chelators described in U.S. Pat. No. 4,885,363 and others, as outlined above. Chelators for Dy+3 (Dy(III)) are also known in the art and described in the references cited herein.

The MRI contrast agents are covalently attached to an optical dye to form the bifunctional detection agents of the invention. By "optical dye" herein is meant a photoluminescent compound. That is, a compound that will emit detectable energy after excitation with light. In a preferred embodiment, the optical dye is fluorescent; that is, upon excitation with a particular wavelength, the optical dye with emit light of a different wavelength; such light is typically unpolarized. In an alternative embodiment, the optical dye is phosphorescent.

Preferred optical dyes include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red.

Suitable optical dyes are described in the 1989–1991 Molecular Probes Handbook by Richard P. Haugland, hereby expressly incorporated by reference.

In a preferred embodiment, the optical dye is functionalized to facilitate covalent attachment. Thus, a wide variety of optical dyes are commercially available which contain functional groups, including, but not limited to, isothiocyanate groups, amino groups, haloacetyl groups, maleimides, succinimidyl esters, and sulfonyl halides, all of which may be used to covalently attach the optical dye to a second molecule, such as the MRI contrast agents or linkers used in the present invention.

The choice of the functional group of the optical dye will depend on the site of attachment to the MRI contrast agent or linker, as outlined below.

The covalent attachment may be either direct or via a linker. In one embodiment, a carboxylic "arm" of an MRI contrast agent is used as a chemically active functional group to attach the MRI agent to a chemically functionalized optical dye, without a linker or spacer. Alternatively, there is a group between the MRI agent and optical dye that serves to link the two together. In one embodiment, the linker is a relatively short coupling moiety, that is used to attach the two. A coupling moiety may be synthesized directly onto an MRI agent for example, and contains at least one functional group to facilitate attachment of the optical dye. Alternatively, the coupling moiety may have at least two functional groups, which are used to attach a functionalized MRI agent to a functionalized optical dye. In an additional embodiment, the linker is a polymer. In this embodiment, covalent attachment is accomplished either directly, or through the use of coupling moieties from the agent or dye to the polymer.

In a preferred embodiment, the covalent attachment is direct, that is, no linker is used. In this embodiment, the MRI contrast agent preferably contains a carboxylic acid which is used for direct attachment to the functionalized optical dye, such as is depicted below in Structure 5. Thus, for example, for direct linkage to a carboxylic acid group of a MRI contrast agent such as DOTA or DTPA, amino modified or hydrazine modified optical dyes will be used for coupling via carbodiimide chemistry, for example using 1-ethyl-3-(3-dimethylaminopropyl)-carbodiimide (EDC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the optical dye, such as is commercially available. Alternatively, the anhydride form of the MRI contrast agent such as DTPA or DOTA may be coupled to the amino modified optical dye, as is described herein.

Structure 5 depicts a direct covalent attachment between the MRI contrast agent (in this embodiment, unsubstituted DOTA, although as will be appreciated both substituted DOTA as well as other MRI agents such as unsubstituted or substituted DTPA may be used) and a functionalized optical dye. As will be appreciated by those in the art, other MRI agents may also be used. Additionally, Structure 5 depicts a carbonyl link between the optical dye and the MRI agent, which may include an ester linkage or other linkages depending on the functionality of the optical dye.

Structure 5

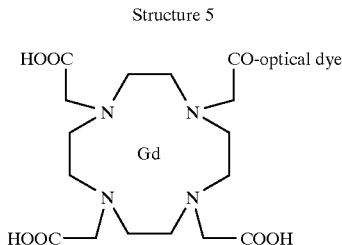

In a preferred embodiment, the bifunctional detection agents of the invention utilize a linker. By "linker" herein is meant either a coupling moiety or a polymer. In general, the embodiments utilizing a coupling moiety result in bifunctional detection agents that are less than about 2–3 MW, with less than about 2 being preferred and less than about 1 being particularly preferred. Similarly, embodiments utilizing polymers as the linkers result in bifunctional detection agents that range from about 2 MW to about 100 MW, with from about 2 to about 50 MW being preferred and from about 2 to about 10 being particularly preferred.

The choice of the linker will effect the functionality of the optical dye. In a preferred embodiment, the optical dye is attached to an amine group on a linker, which in turn is covalently attached to the MRI contrast agent. In this embodiment, the optical dye is functionalized with an amine-reactive group, such as an isothiocyanate (set 4 of the Molecular Probes catalog, supra), a succinimidyl ester (set 5 of the Molecular Probes catalog, supra), a sulfonyl halide (set 6 of the Molecular Probes catalog, supra), or others. Particularly preferred are the isothiocyanate derivatives, such as fluoroscein isothiocyanate (FITC), rhodamine X isothiocyanate (XRITC), and tetramethylrhodamine isothiocyanate (TRITC).

In an additional preferred embodiment, the optical dye is attached to a thiol group on the linker, which is in turn covalently attached to the MRI contrast agent. In this embodiment, the optical dye is functionalized with a thiol-reactive group such as a haloacetyl derivative (particularly iodoacetamides; set 1 of the Molecular Probes catalog), a maleimide (particular N-ethylmaleimide; set 2 of the Molecular Probes catalog), or others.

In a preferred embodiment, the linker is a coupling moiety. A "coupling moiety" is capable of covalently linking two or more entities. One end of the coupling moiety is attached to the MRI contrast agent, and the other is attached to the optical dye. In a preferred embodiment, the coupling moiety is attached first to either a MRI contrast agent or an optical dye, and then a functional group of the coupling moiety is used to attach the second moiety. In this embodiment, a functional group may not be required to attach to the MRI agent, for example, and thus the coupling moiety contains at least one functional group to facilitate attachment. Suitable functional groups include, but are not limited to, amines, thiols, and carboxylic acids. In another embodiment, the coupling moiety is bifunctional, and utilizes a functional group for attachment to both the MRI agent and the optical dye.

The functional group(s) of the coupling moiety are generally attached to additional atoms, such as alkyl or aryl groups, to form the coupling moiety. Oxo linkers are also preferred. As will be appreciated by those in the art, a wide range of coupling moieties are possible, and are generally only limited by the ability to synthesize the molecule and the reactivity of the functional group. For example, a preferred embodiment synthesizes a MRI agent with a coupling moiety attached, to which the optical dye is then subsequently attached via the functional group of the coupling moiety. For example, for DOTA derivatives, both nitrogen substitution (Structure 2) or carbon substitution (Structure 1) of the cyclen ring backbone is possible with a wide variety of groups. See for example U. S. Pat. Nos. 4,885,363 and 5,358,704 (nitrogen substitution) and Moi et al., J. Am. Chem. Soc. 110:6266–6267 (1988) (carbon substitution), and Chang et al., Applications of Methods and Radiochemistry, Gergamon Press: New York 1982, Lambrecht et al., Ed.

Generally, the coupling moiety comprises at least one carbon atom, due to synthetic requirements; however, in some embodiments, the coupling moiety may comprise just the functional group.

In a preferred embodiment, the coupling moiety comprises additional atoms as a spacer. As will be appreciated those in the art, a wide variety of groups may be used. For example, a coupling moiety may comprise an alkyl or aryl group substituted with one or more functional groups. Thus, in one embodiment, a coupling moiety containing a multiplicity of functional groups for attachment of multiple MRI contrast agents and optical dyes may be used, similar to the polymer embodiment described below. For example, branched alkyl groups containing multiple functional groups may be desirable in some embodiments.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to 100 carbon atoms (C1–C100), with a preferred embodiment utilizing from about 2 to about 50 carbon atoms (C2–C50), with about C2 through about C10 being preferred. Also included within the definition of an alkyl group are cycloalkyl groups such as C5 and C6 rings, and heterocyclic rings with nitrogen, oxygen, sulfur or phosphorus. Additional suitable heterocyclic substituted rings are depicted in U.S. Pat. No. 5,087,440, expressly incorporated by reference. In some embodiments, two adjacent R groups may be bonded together to form ring structures together with the carbon atoms of the chelator, such as is described in U.S. Pat. 5,358,704, expressly incorporated by reference. These ring structures may be similarly substituted.

By "aryl" group herein is meant aromatic rings such as phenyl and heterocyclic aromatic rings such as pyridine, furan, thiophene, pyrrole, indole and purine.

In addition to the functional group used to covalently attach the contrast agents, the alkyl and aryl groups may be further substituted by either additional functional groups or other atoms. For example, a phenyl group may be a substituted phenyl group. Suitable substitution groups include, but are not limited to, halogens such as chlorine, bromine and fluorine, amines, hydroxy groups, carboxylic acids, nitro groups, carbonyl and other alkyl and aryl groups. Thus, arylalkyl and hydroxyalkyl groups are also suitable for use in the invention.

Preferred coupling moieties include, but are not limited to, alkyl and aryl amines, such as aminobenzyl (particularly p-aminobenzyl) and amino-benzyl derivatives, and alkyl and aryl thiols, and oxo groups. Particularly preferred bifunctional detection agents utilizing these coupling moieties are depicted below in Structures 6 (with otherwise unsubstituted DOTA as the MRI agent, p-aminobenzyl as the coupling moiety, and rhodamine as the optical dye), 7 (with otherwise unsubstituted DOTA as the MRI agent, aminopropyl as the coupling moiety, and rhodamine as the optical dye) and 8 (with otherwise unsubstituted DOTA as the MRI agent, methoxyamine as the coupling moiety, and rhodamine as the optical dye):

Structure 6

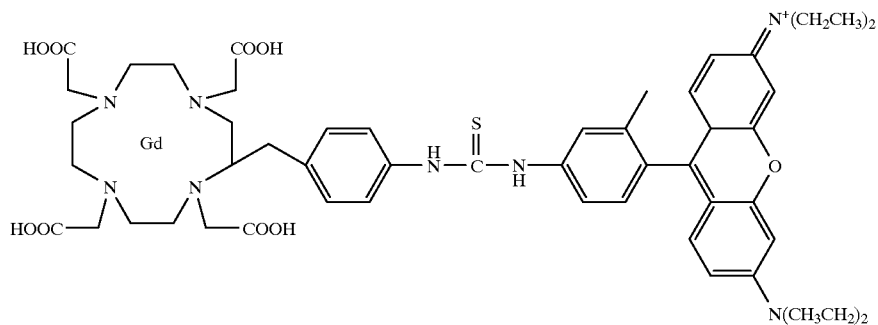

Structure 7

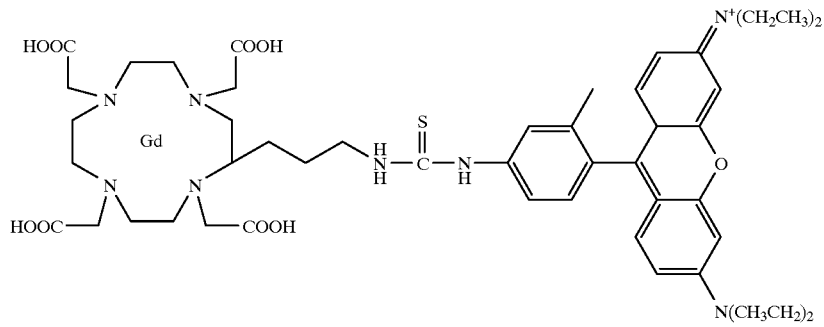

Structure 8

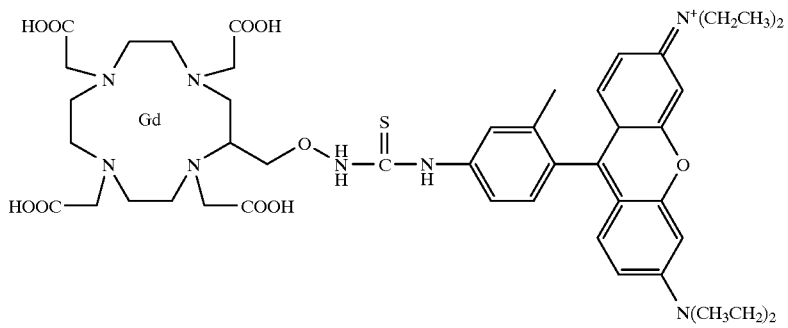

Thus, in a preferred embodiment, the bifunctional detection agents of the present invention utilize a coupling moiety, depicted herein as "X" with a covalently attached to an optical dye. The coupling moiety is attached either via a carboxylic "arm" of the MRI agent (exemplified by DOTA below, although any of the other MRI agents such as DTPA may also be used), as depicted in Structure 9, via a backbone carbon of the chelator of the MRI agent, as depicted in Structure 10, or at a backbone nitrogen, as depicted in Structure 11:

Structure 9

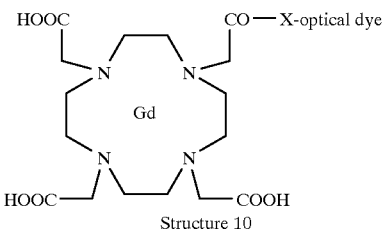

Structure 10

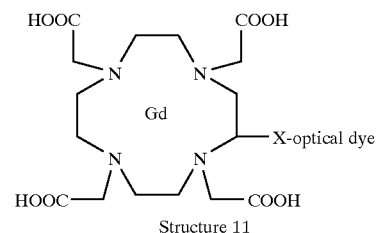

Structure 11

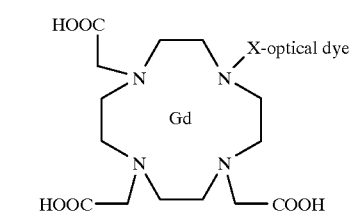

As noted above, the MRI agent may contain additional substitution groups.

Particularly preferred examples of this embodiment utilize DOTA as the MRI agent, p-aminobenzyl, methoxyamine, and aminobutyl as the X linker, and fluoroscein and rhodamine as the optical dye (isothiocyanate derivatives).

In a preferred embodiment, the linker comprises a polymer. As used herein, a "polymer" comprises at least two or three subunits, which are covalently attached. At least some portion of the monomeric subunits contain functional groups for the covalent attachment of MRI contrast agents and optical dyes. In some embodiments coupling moieties are used to covalently link the subunits with the MRI agent or optical dye. Preferred functional groups for attachment are amino groups, carboxy groups, oxo groups and thiol groups, with amino groups being particularly preferred. As will be appreciated by those in the art, a wide variety of polymers are possible. Suitable polymers include functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

In a preferred embodiment, the polymer contains a single type of functional moiety for covalent attachment. In this embodiment, both the MRI contrast agent and the optical dye are attached using the same functionality. In this embodiment, as is outlined herein, some portion of the subunits contain MRI agents, some portion contains optical dyes, and generally some portion of the subunits do not contain either, as is more fully described below. As will be described herein, in some instances the unreacted functional groups are protected or "capped" to neutralize the functionality, i.e. from undesirable side reactions or excess charge, as is described below.

In this embodiment, every monomeric subunit may contain the same functional moiety, or alternatively some of the subunits comprise a functional moiety and others do not. Thus, for example, polylysine is an example of a polymer in which every subunit comprises an amino functional group. Polyamino acids comprising lysine and alanine are an example of polymers in which some of the subunits do not comprise a chemically reactive functional moiety, as the alanine amino acids do not contain a functional moiety that can be used to covalently attach either MRI agents or optical dyes, and thus do not need to be protected.

In a preferred embodiment, the polymer comprises different, i.e. at least two, functional groups. Thus for example, polystyrene with amino and thiol functional groups can be made or polyamino acids with two functional groups, such as polymers comprising lysine (ε-amino functional group) and glutamic acid (carboxy functional group). In this embodiment, one functionality is used to add the MRI contrast agent and the other is used to add the optical dye. Polymers can be generated that contain more than two functionalities as well.

In this embodiment, as described above, it is also possible to incorporate monomeric subunits that do not contain a functional moiety, for example, to avoid the use of protecting groups, i.e to decrease toxicity as outlined herein.

The length of the polymer can vary widely. As will be appreciated by those in the art, the size of the bifunctional detection agent will affect the membrane permeability of the agent. Generally, the larger the agent, the less membrane permeable. However, bifunctional detection agents which are quite large may tend to aggregate in cells over time, and thus may not be desirable in some embodiments. The size of the bifunctional detection agent will depend on the length of the polymer and the number of MRI agents and optical dyes per polymer. Generally, the bifunctional detection agents utilizing polymers range from about 4 to about 50,000 MW, with from about 3,000 to about 30,000 being preferred, and from about 5,000 to about 25,000 being particularly preferred.

The smallest polymer has two or three monomeric subunits, (n=2 or n=3) one of which has an MRI contrast agent covalently attached, and another of which has an optical dye covalently attached. Preferably, a third monomeric subunit is between them, to minimize unnecessary steric interactions, although this is not required. Generally, as outlined above, the length of the polymer is determined by the total molecular weight of the bifunctional detection agent, rather than the absolute number of monomeric subunits. However, preferred polymers include from about 10 to about 1000 monomeric subunits, with from about 20 to about 500 being preferred and from about 30 to about 400 being particularly preferred.

The number of MRI agents covalently attached per polymer can vary widely, and will depend in part on the synthetic conditions chosen. Without being bound by theory, it appears that to visualize an individual cell using an MRI contrast agent, at least approximately 1,500 Gd(III) ions are preferred. Thus, both the quantity of the bifunctional detection agent, and the amount of MRI contrast agent molecules per polymer, can be varied to allow suitable amounts to be used. In general, the mole % of monomeric subunits containing covalently attached MRI agents can vary from less than 1 mole % to over 99 mole %, with from about 20 mole % to about 50 mole % being preferred, and from about about 10mole % to about 40mole % being particularly preferred.

Similarly, the number of optical dyes covalently attached per polymer can also vary widely. In general, the mole % of monomeric subunits containing covalently attached optical dyes can vary from less than 1 mole % to over 99 mole %, with from about 20 mole % to about 50 mole % being preferred, and from about about 10mole % to about 40mole % being particularly preferred.

In a preferred embodiment, chemically reactive functional groups of the polymer which do not contain either an MRI agent or an optical dye are "capped" or "protected" with a "protecting group" to neutralize the functionality. For example, polylysine may be toxic to cells, due to the excessive charge; thus unreacted amino groups are preferably neutralized. The choice of the protecting group will depend on the functionality to be neutralized. Protecting groups are well known in the art; see for example, Greene, Protecting Groups in Organic Synthesis, John Wiley & Sons, 1991, hereby incorporated by reference. When the functionality is an amino group, a preferred protecting group is β-propiolactone.

In one embodiment, the bifunctional detection agents of the invention that utilize polymers may also utilize coupling moieties (depicted herein as X) to attach the polymers to either the MRI agents or the optical dyes or both. That is, a coupling moiety may be used to facilitate attachment of the MRI agents and/or optical dyes to the polymer.

The bifunctional detection agents of the invention are synthesized as follows.

Direct covalent attachment of an MRI agent and an optical dye may be accomplished in several ways. A carboxylic acid group of a chelating component of an MRI contrast agent such as DOTA or DTPA is directly linked to an amino modified or hydrazine modified optical dyes via carbodiimide chemistry, for example using 1-ethyl-3-(3-dimethylaminopropyl)-carbodiimide (EDC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the optical dye, such as is commercially available. Alternatively, the anhydride form of the MRI contrast agent such as DTPA or DOTA may be coupled to the amino modified optical dye as is outlined in the Examples.

When a coupling moiety is used as a linker, the synthesis can proceed in several ways. In a preferred embodiment, the MRI contrast agent is synthesized containing the coupling moiety, and then the functional group of the coupling moiety is used to attach the optical dye. For example, for DOTA derivatives, both nitrogen substitution (Structure 2) or carbon substitution (Structure 1) of the cyclen ring backbone is possible with a wide variety of groups. See for example U.S. Pat. Nos. 4,885,363 and 5,358,704 (nitrogen substitution) and Moi et al., J. Am. Chem. Soc. 110:6266–6267 (1988) (carbon substitution). Similarly, DTPA may also be altered at either of these positions as well, see for example Chang et al., supra.

When a polymer is used as the linker, the synthesis can proceed in a number of ways, depending on the functional groups chosen. In a preferred embodiment, an excess of the anhydride form of the MRI agent such as DOTA or DTPA is reacted with a polymer containing an amino functionality such as polylysine. The amount of the excess will drive the amount of MRI agent covalently attached to the polymer. Thus, as is outlined in the examples, using a 50×excess of DTPA anhydride to polylysine of n=171 results in roughly 5 to 60 DTPA molecules per polymer. A 100× excess results in from about 5 to about 20 DTPAs per polymer, a 200× excess results in about 25 DTPAs, and a 400X excess results in roughly 35 DTPAs per polymer. In this embodiment, the concentration of the polylysine is kept low to avoid crosslinking that may occur at higher concentrations.

Alternatively, the MRI agents and/or optical dyes may be functionalized or contain a coupling moiety, and then added to the polymer using the techniques disclosed herein.

Once the MRI agent is covalently attached, the optical dye is attached, generally through the use of an isothiocyanate derivative if the polymer contains amino functionalities.

After the MRI agents and optical dyes are attached, unreacted functional groups may be protected, if necessary. For example, amino groups may be protected using β-propyllactone, or other protecting groups. This may be necessary to detoxify the polymer. Thus, for example, the high charge of polylysine may render it toxic to cells; thus the excess charge can be neutralized.

Additionally, the charge of the bifunctional detection agent may be altered for membrane permeability. Generally, charged molecules are impermeable, with neutral compounds being significantly more permeable. In a preferred embodiment, the bifunctional detection agent is membrane impermeable. Thus, in this embodiment, one of the carboxylic acid "arms" of either DOTA or DTPA is used for attachment, since in the presence of the Gd(III) this renders the MRI agent neutral.

Once made, the bifunctional detection agents of the invention find use in a number of applications. In a preferred embodiment, the bifunctional detection agents are used to image cells or tissues in the same way that optical dyes and MRI agents are used, as is well known in the art. Thus, they are administered either to a cell, tissue or organism and detected using known optical and MRI detection methods. Since MRI agents are optically silent, these agents may be traced via the attachment to the optical dye. The uses of these agents will be obvious to those skilled in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

DOTA linked via a coupling moiety to rhodamine

I. General.

All solvents and reagents for organic synthesis were obtained from Aldrich or Fluka and used without further purification. Tetramethylrhodamine-5-isothiocyanate (TRITC) was obtained from Molecular Probes. Distilled-deionized water was obtained from a NANOpure water purification system and was used throughout to minimize trace-metal contamination of the ligands and chelates. Reactions were performed in oven-dried flasks under positive argon pressure and monitored by analytical thin-layer chromatography (TLC) using E.Merck silica gel 60F plates (0.25 mm). E.Merck silica gel (230–400 mesh) was used for flash chromatography. 1H and 13C NMR spectra were recorded at 300 MHz on a GE300 NMR spectrometer. Analytical HPLC was performed with a Waters 600E Liquid Chromatograph using a reverse phase VYDAC 201HS54 4.6 mm×25 cm 5 micron C18 column. The samples were injected onto the C18 reverse phase column and eluted with 100 mM triethylammonium acetate with a gradient of 1–20% acetonitrile at a flow rate of 1 mL/min. The products were detected by UV absorption at 260 and 330 nm. The fluorescence of gadolinium-containing compounds was analyzed on a Hitachi F-4500 instrument (excitation at 280 nm, emission ranged from 313 to 335 nm). Spin-lattice relaxation time (T1) measurements were obtained on a relaxometer operating at a fixed magnetic field. T1 was determined for different Gd-complex concentrations (0.1–10 mM) in weakly buffered medium (100 mM sodiumcarbonate) at varying pH (pH 7, 8 and 9).

II. Synthesis of various ligands 2-(p-Aminobenzyl)-1,4,7,10-tetraazacyclododecane-N,N',N",N"'-tetraaceticacid 1 (PABD). The synthesis of PABA was performed as described in the literature (McMurray et al., Bioconjugate Chem. 3:108–117 (1992); Garrity et al., Tet. Lett. 34:5531–5534 (1993); Takenouchi et al., J. Org. Chem. 58:6895–6899 (1993); Ansari et al., Bioorg. & Med. Chem. 3:1067–1070 (1993); Renn et al., Bioconjugate Chem. 3:563–569 (1992).

Gd(PABD). Method A. To a stirred solution of p-aminobenzyl-DOTA in either water or 100 mM sodium-carbonate (pH 8) was added gadoliniumchloride (0.99 eq). The reaction mixture was allowed to stir at 80° C. for 12 h. The solution was then concentrated to near dryness, redissolved in 100 mM triethylammoniumacetate/acetonitrile and purified by ETLC chromatography. Method B. To a stirred solution of p-aminobenzyl-DOTA in either water or 100 mM sodiumcarbonate (pH 8) was added gadoliniumoxide (1.3 eq). The reaction mixture was allowed to stir at 80° C. for 18 h. The solution was filtered through an Acrodisc (LC 13 PVDF, 0.2 mm) to remove unreacted gadoliniumoxide. The solution was then concentrated to near dryness, redissolved in 100 mM triethylammoniumacetate/acetonitrile and purified by HPLC chromatography.

2-(4-Aminobutyl)-1,4,7,10-tetraazacyclododecane-N,N',N",N"'-tetraacetic acid 2 (Lys-DOTA). The synthesis of Lys-DOTA was performed as described in the literature (Crivici et al., Syn. Comm. 23:49–53 (1993); Cox et al., J. Chem. Soc. Perkin Trans. I 1990 p2567.

Ligand 3

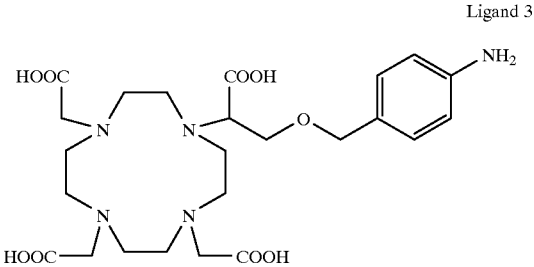

Ethyl-2,3-dibromopropionate 4 0.95 ml (6.53 mmol) was added to a mixture of 4-nitrobenzylalcohol 5 (1 g, 6.53 mmol) and anhydrous potassiumcarbonate 1.1 g (7.8 mmol) in anhydrous acetonitrile and the reaction mixture was stirred for 12 h at 70° C. The reaction mixture was then allowed to cool down to room temperature, concentrated to a smaller volume and diluted with dichloromethane. The combined organic layers were washed with 0.5 N $NaH_2PO_4$ solution and brine, and dried over magnesiumsulfate. Concentration of the solution followed by purification by flash chromatography (methylenechloride/hexane, 4:1) provided the desired product 3-(4-nitrobenxyloxy)-2-bromopropionic acid 6.

To a stirred solution of cyclen 7 (100 mg, 0.58 mmol) was slowly added 3-(4-nitrobenxyloxy)-2-bromopropionic acid 6 (128 mg, 0.39 mmol). The solution was stirred at 50° C. for 48 h. The resulting solution was concentrated to dryness and the residue was suspended in water, acidified with HCl to pH 2.5 and extracted with chloroform. The aqueous phase (neutralized by addition with 1N KOH) was loaded onto an Amberlite IR 120 cation-exchange-column (H+form). The column was first eluted with water to neutrality followed by elution of the product 8 with 4N $NH_4OH$.

To a stirred solution of the modified cyclen 8 (100 mg, 0.24 mmol) in water was added a solution of bromoacetic acid 9 (197 mg, 1.42 mmol) and an equimolar amount of KOH (80 mg, 1.42 mmol) in water. The resulting solution was brought to pH 10 with a 7M KOH solution and was stirred at 80 C for 12 h. During this time the pH was maintained at 10 by adding additional KOH solution. After 12 h the mixture was cooled to room temperature, and the product was isolated by acidification (pH 10) with conc. HBr. The crude product was filtered off and purified by cation-exchange chromatography and HPLC. The final product 3 was obtained by quantitative reduction of the nitro-group to the amine using Lindlar catalyst in ethanol.

III. Coupling to an optical agent.

Gd(Rhoda-DOTA). To stirred solution of Gd(PABA) (1 mg, 1.46 mmol) in 250 ml N,N-dimethylformamide was added TRITC (0.72 mg, 1.61 mmol, 1.1 eq). The solution was covered with aluminium foil and allowed to stir at room temperature for 10 h. The solution was then concentrated to dryness, taken up in 100 mM sodiumcarbonate/acetonitrile and purified by HPLC chromatography.

Example 2

DTPA linked via polylysine to rhodamine

Modification of Poly-d-lysine (pdl) with DTPA and rhodamine Pdl (4,25,53k) was purified by FPLC on a superdex 75 gel filtration column. Derivitized polymers of 7 to 36 DTPA molecules/polylysine were obtained by successively increasing the excess of DTPA anhydride at ratios of 100×, 200× and 400× DTPA anhydride to polylsine. The purified ratio of 1 DTPA per 3–4 lysine monomer units was obtained regardless of the molecular weight of the polymer.

1) Attachment of DTPA to pdl (in 400 molar excess of DTPA to pdl): At ambient temperature, native pdl was dissolved with stirring in buffer (0.5 $NaHCO_3$, pH 9.7). DTPA anhydride was added slowly and allowed to react for 45 minutes with stirring. The product was purified over gel filtration (Sephadex 75) using a Pharmacia FPLC system and speedvacced overnight.

2) Chelation of $Gd^{3+}$ to TRITC-G-DTPA-pdl:

In a 75° C. oil bath with stirring, $GdCl_3$ (0.1 ml of a 5.3 mg/ml solution of $GdCl_3$ in $H_2O$) was added slowly to TRITCG-DTPA-pdl compound dissolved in $H_2O$. The reaction proceeded for 1 hour, then was purified via gel filtration using a Sephadex G-25 PD 10 column pre-equilibrated with water and overnight.

3) Attachment of TRITC-G to DTPA-pdl (in 30 molar excess of TRITC-G to DTPA-pdl):

At ambient temperature, Gd-DTPA-pdl was dissolved in a minimum of $H_2O$ or DMF. TRITC-G was dissolved in DMF (or $H_2O$) (0.5 ml DMF for 5 mgs TRITC-G) to form an opaque slurry. This slurry was added over 10 minutes with stirring to the DTPA-pdl, along with a 0.2 ml of rinse of buffer. The reaction proceeded with stirring for 2 hours. The product was purified via gel filtration using a Sephadex G-25 PD 10 column pre-equilibrated with water, then speedvacced overnight.

4) β-propiolactone capping

In order to render the double score agent nontoxic when injected directly into cells the GdDTPA-Rhodamine-Poly-d-Lys was reacted with β-propiolactone with only minor modification to a published procedure (see U.S. Pat. No. 3,907,755. This reaction efficiently transforms the ɛnitrogens of the lysine derivatives to OH groups, and subsequent toxcity studies confirmed the success of the procedure.

Xenopus lavevis embryo at stage 8 was injected with GRIP into the marginal blastomere at the 16 cell stage. The labelled cells populate the prosepective mesodermal regions as seen in confocal fluorescence image (data not shown). The distribution of labelled cells is confirmed using MRI and delineate cells that are unobservable by fluorscence techniques (data not shown). The progeny of the labeled blastomere at 5 days later at stage ·38–39 were imaged (data not shown), and labeled cells in somitic mesoderm were clearly visible and span the length of each somitic block as expected. Several cells in endoderm are also labeled, which is in agreement with published fate maps of 16 cell stage embryos.

I claim:

1. A bifunctional detection agent comprising a polymer covalently linked to at least one optical dye and at least one MRI contrast agent.

2. A polymer comprising a first subunit covalently attached to an MRI agent, and a second subunit covalently attached to an optical contrast agent.

3. A polymer according to claim 2 further comprising a third subunit.

4. A polymer according to claim 2 wherein said first and second subunits are the same.

5. A polymer according to claim 2 wherein said first and second subunits are different.

6. A bifunctional detection agent according to claim 1 or 2 wherein said optical dye is selected from the group consisting of fluorescein, rhodamine, tetramethylrhodamine, eosin, erythrosin, coumarin, methyl-coumarins, pyrene, Malacite green, stilbene, Lucifer Yellow, Cascade Blue™, and Texas Red.

7. A bifunctional detection agent according to claim 6 wherein said optical dye is fluorescein.

8. A bifunctional detection agent according to claim 6 wherein said optical dye is rhodanine.

9. A bifunctional detection agent according to claim 1 or 2 wherein said MRI contrast agent is selected from the group consisting of 1,4,7,10-tetraazacyclododecane-N,N',N"N"'-tetracetic acid (DOTA), substituted DOTA, diethylenetriaminepentaacetic (DTPA), substituted DTPA, 1,4,7,10-tetraazacyclododecane-N,N', N", N"'tetraethylphosphorus (DOTEP), substituted DOTEP, 1,4,7,10-tetraazacyclododecane-N,N',N"-triacetic acid (Do3A), and substituted Do3A.

10. A bifunctional detection agent according to claim 9 wherein said MRI contrast agent is DOTA.

11. A bifunctional detection agent according to claim 9 wherein said MRI contrast agent is DTPA.

12. A bifunctional detection agent according to claim 1 or 2 wherein said polymer is a functionalized dextran.

13. A bifunctional detection agent according to claim 1 or 2 wherein said polymer is a polyamino acid.

14. A bifunctional detection agent according to claim 13 wherein said polyamino acid is polylysine.

15. A bifunctional detection agent according to claim 1 or 2 wherein said polymer has a molecular weight of less than 40 kD.

16. A bifunctional detection agent according to claim 1 or 2 wherein said polymer has a molecular weight of less than 25 kD.

17. A bifunctional detection agent according to claim 1 or 2 wherein said polymer has a molecular weight of less than 15 kD.

18. A bifunctional detection agent according to claim 1 or 2 wherein said polymer has a molecular weight of less than 10 kD.

19. A method of visualizing a cell, tissue or organism comprising administering a bifunctional detection agent according to claim 1 or 2 and optically visualizing said cell, tissue or organism.

20. A method of visualizing a cell, tissue or organism comprising administering a bifunctional detection agent according to claim 1 or 2 and visualizing said cell, tissue or organism with magnetic resonance imaging.

* * * * *